(12) United States Patent  (10) Patent No.: US 7,160,319 B2
Chouinard et al.  (45) Date of Patent: Jan. 9, 2007

(54) MULTI-SECTION FILAMENTARY ENDOLUMINAL STENT

(75) Inventors: Paul F. Chouinard, Eden Prairie, MN (US); Patrick A. Haverkost, Brooklyn Center, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 571 days.

(21) Appl. No.: 10/366,807

(22) Filed: Feb. 14, 2003

(65) Prior Publication Data

US 2003/0149473 A1  Aug. 7, 2003

Related U.S. Application Data

(62) Division of application No. 09/442,165, filed on Nov. 16, 1999, now Pat. No. 6,585,758.

(51) Int. Cl.
*A61F 2/06* (2006.01)
*A61M 29/00* (2006.01)

(52) U.S. Cl. .................................... 623/1.16
(58) Field of Classification Search ...... 623/1.15–1.22; 606/108, 198, 191, 194, 195
See application file for complete search history.

(56) References Cited

U.S. PATENT DOCUMENTS

| 4,655,771 A | 4/1987 | Wallsten |
| 5,019,090 A | 5/1991 | Pinchuk |
| 5,061,275 A * | 10/1991 | Wallsten et al. ............ 623/1.22 |

(Continued)

FOREIGN PATENT DOCUMENTS

EP  0 796 597  9/1997

(Continued)

*Primary Examiner*—Vy Q. Bui
(74) *Attorney, Agent, or Firm*—RatnerPrestia

(57) ABSTRACT

A multi-section filamentary stent comprises a braided section, which is a cylindrical mesh of a first set of filaments, connected to at least one wound section comprising a second set of one or more filaments having a repeating configuration with a bent portion. The two sections are preferably connected by at least one continuous filament extending into both sections. The two sections may be connected by a weld, a suture, a common graft, an overlapping portion of the two sections, or one or more filaments of one section looping through portions of the other section. The stent may comprise a first section, having a braided first stent architecture with a first flexibility and a first radial force, and a second section, having a non-braided second stent architecture with a second flexibility less than the first flexibility and a second radial force greater than the first radial force, in which at least one continuous filament is integral to both the first and second sections. The stent may have a radially compressed configuration and a radially expanded configuration, in which the first section has a first shortening ratio, and the second section has a second shortening ratio less than the first shortening ratio. Such multi-section stents may comprise modular components of a modular stent, such as a bifurcated modular stent, adapted for joining together in situ. The multi-section stent may comprise a first section having a first percentage of open area and a second section having a second percentage of open area. The stent may also comprise a first section having a first stent architecture with an end effect wherein the radial strength at the end is less than elsewhere in the stent, and a second section having a second stent architecture to counteract the end effect. Methods for treating body lumen by implanting the stents as described herein are also disclosed, as is a method for counteracting a stent architecture end effect.

11 Claims, 9 Drawing Sheets

U.S. PATENT DOCUMENTS

| | | |
|---|---|---|
| 5,135,536 A | 8/1992 | Hillstead |
| 5,282,824 A | 2/1994 | Gianturco |
| 5,292,331 A | 3/1994 | Boneau |
| 5,354,308 A | 10/1994 | Simon et al. |
| 5,383,892 A | 1/1995 | Cardon et al. |
| 5,395,390 A | 3/1995 | Simon et al. |
| 5,507,767 A | 4/1996 | Maeda et al. |
| 5,540,712 A | 7/1996 | Kleshinski et al. |
| 5,591,229 A | 1/1997 | Parodi |
| 5,643,339 A | 7/1997 | Kavteladze et al. |
| 5,649,949 A | 7/1997 | Wallace et al. |
| 5,693,086 A * | 12/1997 | Goicoechea et al. ....... 623/1.11 |
| 5,746,765 A * | 5/1998 | Kleshinski et al. ......... 128/898 |
| 5,746,766 A | 5/1998 | Edoga |
| 5,755,778 A | 5/1998 | Kleshinski |
| 5,776,162 A | 7/1998 | Kleshinski |
| 5,800,515 A | 9/1998 | Nadal et al. |
| 5,817,126 A * | 10/1998 | Imran ....................... 623/1.15 |
| 5,827,321 A | 10/1998 | Roubin et al. |
| 5,938,697 A | 8/1999 | Killion |
| 6,059,822 A | 5/2000 | Kanesaka et al. |
| 6,143,016 A * | 11/2000 | Bleam et al. ............... 606/198 |
| 6,146,403 A | 11/2000 | St. Germain |
| 6,179,867 B1 | 1/2001 | Cox |
| 6,344,056 B1 | 2/2002 | Dehdashtian |

FOREIGN PATENT DOCUMENTS

| | | |
|---|---|---|
| EP | 0 830 853 | 3/1998 |
| EP | 0 880 948 | 12/1998 |
| FR | 2 765 097 | 6/1997 |
| WO | WO 99/44535 | 9/1999 |
| WO | WO 00/19943 | 4/2000 |

* cited by examiner

MULTI-SECTION FILAMENTARY ENDOLUMINAL STENT

CROSS-REFERENCE TO RELATED APPLICATIONS

The application is a divisional of U.S. application Ser. No. 09/442,165 Nov. 16, 1999, now U.S. Pat. No. 6.585,758.

TECHNICAL FIELD

This invention relates generally to endoluminal stents, grafts, and/or prostheses and, more specifically, to stents having multiple longitudinal sections of different stent architecture.

BACKGROUND OF THE INVENTION

A stent is an elongated device used to support an intraluminal wall. In the case of a stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft.

A prosthesis may be used, for example, to treat a vascular aneurysm by removing the pressure on a weakened part of an artery so as to reduce the risk of rupture. Typically, a prosthesis is implanted in a blood vessel at the site of a stenosis or aneurysm endoluminally, i.e. by so-called "minimally invasive techniques" in which the prosthesis, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the prosthesis to be ejected from the surrounding sheath or catheter in which it is restrained (or alternatively the surrounding sheath or catheter is retracted from the prosthesis), whereupon the prosthesis expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Various types of stent architectures are known in the art, including many designs comprising a filament or number of filaments, such as a wire or wires, wound or braided into a particular configuration. Included among these wire stent configurations are braided stents, such as is described in U.S. Pat. No. 4,655,771 to Hans I. Wallsten and incorporated herein by reference, the '771 Wallsten patent being only one example of many variations of braided stents known in the art and thus not intended as a limitation of the invention described herein later. Braided stents tend to be very flexible, having the ability to be placed in tortuous anatomy and still maintain patency. This flexibility of braided stents make them particularly well-suited for treating aneurysms in the aorta, where often the lumen of the vessel becomes contorted and irregular both before and after placement of the stent.

Braided stents also have several disadvantages, however. One such disadvantage is that the radial strength on the end of the braided stent is typically substantially less than the radial strength in the middle of the stent. Insufficient radial strength on the stent ends can result in an incomplete seal or migration of the device after implantation. Although flaring the ends or covering the stent with a graft can enhance the radial strength of the ends, the radial strength may still be insufficient. Also, when a braided stent is placed around a curve so that the end of the stent terminates within the curve, tapering of the stent end can result. This can also result in poor end sealing and migration. This phenomenon is particularly prevalent in stents greater than 16 mm in diameter. Although such tapering can be minimized by optimizing braid characteristics such as for example, wire count, wire diameter, and end flare, this tapering effect is still of significant concern.

A number of other stent designs are known in the art having greater radial strength but also having less flexibility than braided stents. Such stent designs can be combined with a braided stent design to produce a multi-segment stent having a flexible, braided stent member in the middle and less-flexible, higher-radial-strength stent members on the ends. Referring now to FIG. 18, one known way of combining such stents is merely to implant a braided stent 180 across a region to be repaired (not shown), and then to implant a higher-radial-strength stent 182 overlapping one or both ends 184 of the braided stent to more strongly anchor the braided stent to the lumen (not shown). Such a procedure, however, requires the implantation of multiple stents.

Referring now to FIGS. 1 and 2, it is also known, for example, to attach a braided stent member 2 to radially strong, rigid tubular stent end members 1 and 11. Braided stent member 2 comprises meshing wires 7 that criss-cross to form knots or overlaps 8. Wires 7 of braided stent member 2 are welded to flanges 6 of tubular stent end members 1 and 11 in pairs. This configuration is described in detail in U.S. Pat. No. 5,383,892 to Cardon et al. (hereinafter "Cardon").

In another configuration, described in detail in U.S. Pat. No. 5,817,126 to Imran, strands or ribbons of metal are attached to opposite ends comprising slotted metal stents. The strands or ribbons are then intertwined to form a braided middle section.

The configuration disclosed in Cardon and Imran, however, while being applicable for providing a braided stent joined to a slotted metal stent, does not address joining a flexible, filamentary braided stent to a more rigid, wound filamentary stent. Filamentary stents of various winding configurations are well-known in the art, having various degrees of flexibility or rigidity. Inasmuch as such wound filamentary stents do not have discrete flanges as shown in FIGS. 1 and 2 and described in Cardon or flat areas of slotted metal for joining ribbons or strands as described in Imran, a wound filamentary stent cannot be joined to a braided filamentary stent as described in Cardon or Imran. It may also be desirable to provide more continuity between the end and middle sections than is offered by the mere welding of the ends of the wires or ribbons of the braided section to flanges or other elements of the slotted metal ends, such welding points potentially forming weak spots in the overall stent construction. Additionally, it may be desired to provide stents with variable radial strength sections having diameters larger than can be readily provided by slotted metal stents. In particular, it is desirable to provide multi-section stents wherein the flexible middle section and the more rigid end sections all comprise filamentary stents.

SUMMARY OF THE INVENTION

According to an embodiment of the invention, a multi-section filamentary stent comprises a braided section, which is a cylindrical mesh of a first set of filaments, and at least one wound section, which is connected to the braided section and which comprises a second set of one or more filaments in a repeating configuration having at least one bent portion. For example, a braided center section may be connected between two wound end sections. The repeating configuration of the second set of filaments in the wound section may comprise: a zig-zag configuration, an overlapping zig-zag configuration, a helical configuration, a non-helical configuration, or a configuration having polygonal cells. The polygonal cells may comprise hexagonal cells or overlapping hexagonal cells. At least one continuous filament may be a member of both the first set of filaments in the braided section and the second set of filaments in the wound section, serving to connect the two sections. In one exemplary configuration, at least one continuous filament may extend from the wound section into the braided section as a redundant filament, a tracer filament, or a redundant tracer filament.

The braided section is preferably connected to the wound section by virtue of at least one of the filaments being a member of both sets of filaments. The sections may also be connected to one another by sutures or welding, by a common graft providing a connection between the braided section and the wound section, or by one or more filaments of the braided section looped around apices of the wound sections, or by at least one filament of the wound section looping around at least one overlap in the braided section. At least a portion of the wound section may overlap and interlock with a portion of the braided section.

According to another embodiment of the invention, a multi-section filamentary stent comprises a first section, having a first stent architecture comprising one or more filaments in a first geometric configuration, and a second section, having a second stent architecture comprising one or more filaments in a second geometric configuration. The first stent architecture has a first flexibility and a first radial strength, and the second stent architecture has a second flexibility less than the first flexibility and a second radial strength greater than the first radial strength. The first stent architecture comprises a braided stent architecture. At least one continuous filament extends into both the first and second sections. The stent may comprise a middle section having the first stent architecture positioned between a distal end section and a proximal end section, each end section having the second stent architecture. The distal end section and the proximal end section may be identical or different in length and/or architecture. In particular, where the distal end is adapted to be positioned in a lumen upstream of the proximal end section relative to intraluminal fluid flow, the length of the distal end may be greater or the architecture may have a greater radial strength than the proximal end.

According to still another aspect of the invention, the stent comprises a first section having a first, braided stent architecture with a first shortening ratio, and a second section having a second stent architecture with a second shortening ratio. The shortening ratio is the length of a section in its radially compressed configuration (typically longer) divided by its length in its radially expanded configuration (typically shorter). The first shortening ratio is greater than the second shortening ratio. The stent comprises at least one continuous filament contained in both the first and second sections.

The invention also comprises various forms of the stent, including a single stent adapted for individual delivery in a body lumen, two or more modular components adapted for joining together in situ in a non-branching lumen, and two or more modular components adapted for joining together in situ in a branching lumen.

A stent according to the present invention may also comprise a first section, having a first, braided stent architecture comprising one or more filaments in a first geometric configuration and having a first percentage of open area, and a second section, having a second stent architecture comprising one or more filaments in a second geometric configuration and having a second percentage of open area greater than the first percentage. The stent comprises at least one continuous filament contained in both the first and second sections. The first section of such a stent may be adapted for deployment in a first portion of a body lumen having no intersecting lumen connected thereto, whereas the second section is adapted for deployment in a second portion of the body lumen having one or more intersecting lumen connected thereto.

A stent according to the present invention may also comprise a first section having a first stent architecture comprising one or more filaments in a first geometric configuration, wherein the first stent architecture has a first radial strength and a known end effect comprising a reduction in radial strength along end lengths of the architecture. A second section of the stent, having a second stent architecture comprising one or more filaments in a second geometric configuration, has a radial strength substantially equal to the first radial strength or at least greater than the radial strength imparted by the end effect, and comprises an end section connected to the first section to counteract the end effect of the first stent architecture.

The present invention further comprises a method of treating a body lumen by implantation of any of the stent structures described herein.

It is to be understood that both the foregoing general description and the following detailed description are exemplary, but are not restrictive, of the invention.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Figure 1:
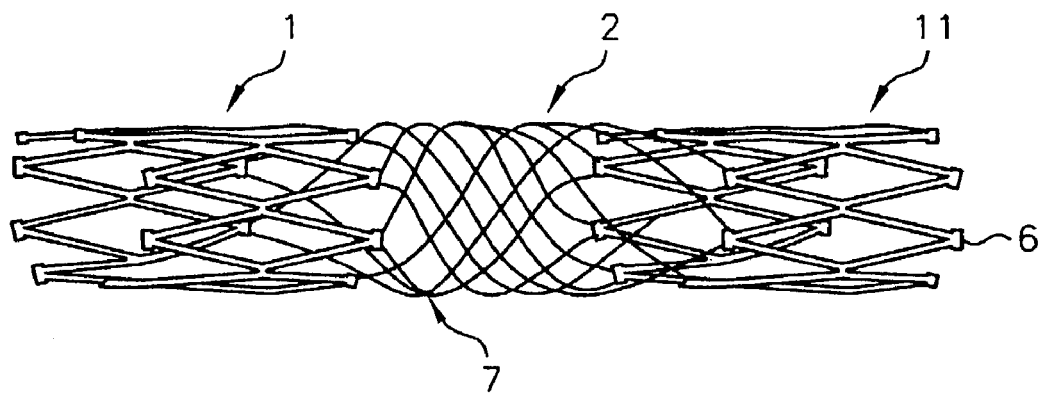
FIG. 1 is a perspective view of a multi-section stent embodiment known in the art.
Figure 2:
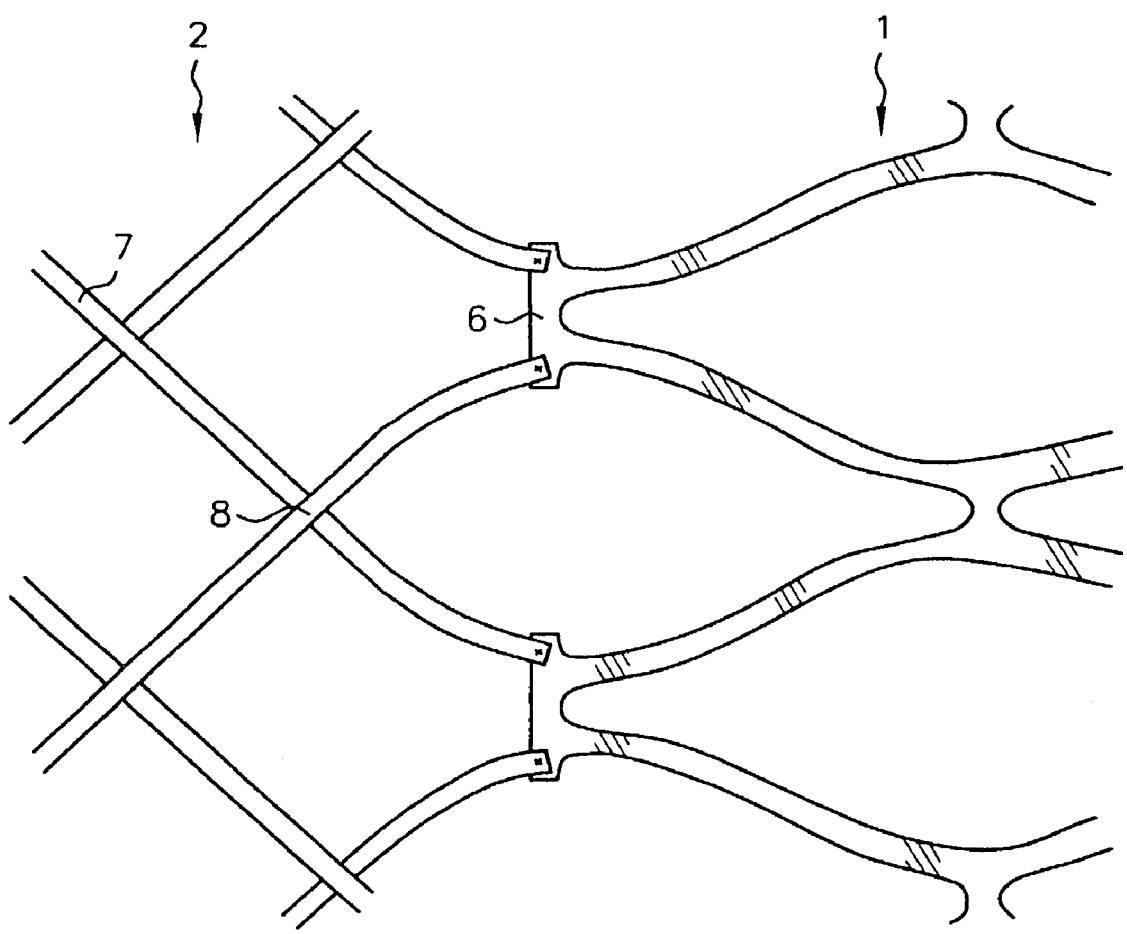
FIG. 2 is an enlarged view of a transition portion between the braided stent architecture section and the laser-cut architecture section of the stent embodiment of FIG. 1.
Figure 3:
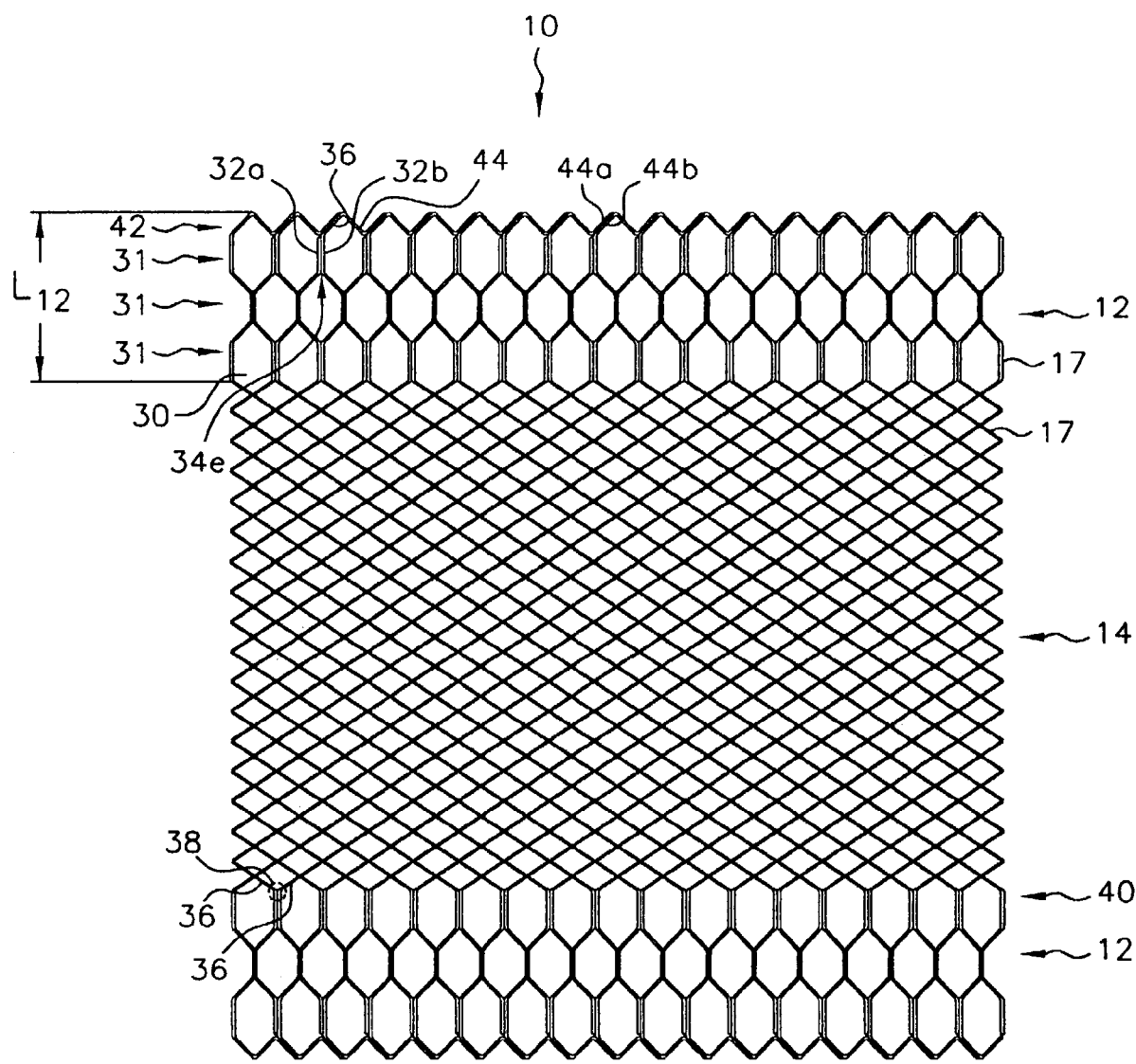
FIG. 3 is an illustration of a stent according to the present invention where the tubular stent has been cut open along a line parallel to the stent axis and flattened.

FIG. 3 shows an exemplary stent embodiment according to the present invention wherein the tubular stent has been cut along a line parallel to the tubular stent axis and flattened. As shown in FIG. 3, stent 10 comprises two end sections 12 and a middle section 14. Middle section 14 has a first stent architecture that comprises a braided stent such as is described in U.S. Pat. No. 4,655,771 to Hans I. Wallsten, and incorporated herein by reference, and end sections 12 have a second stent architecture that comprises a wound stent. End sections 12 have a wound stent architecture comprising one or more filaments in a repeating configuration having at least one bent portion. As shown in FIG. 3, the architecture of wound section 12 is substantially similar to the architectures described in U.S. Pat. Nos. 5,354,308 and 5,395,390 to Simon et al., which are incorporated herein by reference, and described further below. The structures described in the '771 Wallsten patent are merely examples of braided stent architecture, however, just as the structures disclosed in the '308 and '390 Simon patents are merely examples of particular wound stent architectures. None of the structures disclosed in the above named patents, however, are intended to be limiting, as any number of different stent architectures may be used to create multi-section stents in accordance with this invention, as is described in more detail below.

The braided middle section 14 as well as the wound end sections 12 comprise a plurality of filaments 17. Such filaments typically comprise metallic wire, such as nitinol, but may in the alternative comprise bioabsorbable or biostable polymers as are known in the art. The general use of the term "wire" herein is thus not intended as a limitation to metallic wire, but encompasses any type of filament Middle section 14 of stent 10, having the braided stent architecture, has a first flexibility and a first radial strength, and end sections 12, having the wound stent architecture, have a second flexibility less than the first flexibility and a second radial strength greater than the first radial strength. As used herein, "flexibility" or stiffness can be described in terms of the amount of force required to bend a stent into an arc. For example, referring to the schematic representation in FIG. 4, the force f required to bend tubular stent 20 of a particular length into a given arc having a central angle and a given arc radius, is a measure of the stent flexibility. Thus, comparing two stents of equal length with different stent architectures, the stent requiring greater force to bend it into a given arc is relatively stiffer, whereas the stent requiring lesser force is relatively more flexible.

Figure 4:
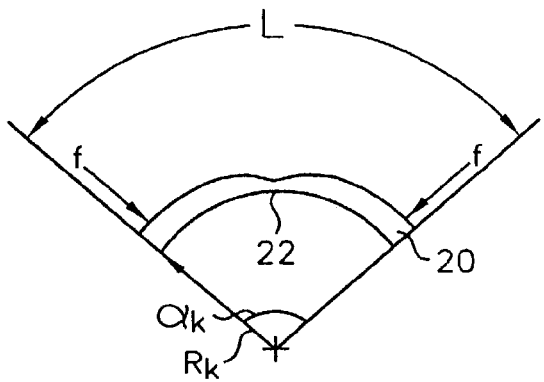
FIG. 4 is a schematic representation of a stent being flexed.

A measure of the "kink resistance" of a stent is the kink angle $\alpha_k$ or kink radius $R_k$ at which the stent kinks (i.e., when the tubular configuration becomes disrupted by crease 22 as shown in FIG. 4). Thus, if one compares the kink angle and kink radius of one tubular stent of a particular length having a first stent architecture to another tubular stent having the same length but a second stent architecture, the stent architecture having a lesser kink radius and a greater kink angle has the most kink resistance. As is well known in the art, it is desirable to provide a stent which has good kink resistance, the extent to which is determined by the degree of tortuosity of the site where the stent will be deployed and, to a lesser extent, the degree of tortuosity of the path to the place of deployment.

As used herein, "radial strength" can be described generally as the resistance of a stent to radial compression. A stent with more radial strength exerts a greater outward radial force when compressed than does a stent with less radial strength. Thus, for example, a shape memory expandable or resiliently compressible stent may have a fully expanded diameter and a constrained diameter as deployed within a lumen. The fully expanded diameter is the diameter to which the stent would expand without any constraint. At the constrained diameter, the stent exerts a radial force F against the lumen, which when distributed over the surface area A of contact between the stent and the lumen can be expressed as a pressure P=F/A in force per unit area. Thus, radial strength can be expressed in terms of radial force or radial pressure. When comparing the radial strength of two stents having different stent architectures, if both stents have the same surface area A of contact (which is the same as having the same contact length where the diameters are equal), radial force may be one proper measure of radial strength. If one stent has a different surface area than the other, however, radial pressure is a more appropriate measure of radial strength. The radial strength and flexibility required depend primarily on the characteristics of the body lumen where the stent is to be deployed, and one skilled in the art can select a desired degree of stent radial strength and/or flexibility based on such characteristics.

Figure 5:
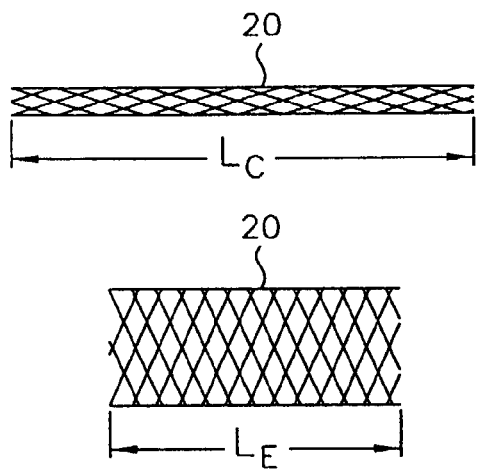
FIG. 5 is a schematic representation of a stent in its compressed state compared to its expanded state, illustrating the shortening of a stent during radial expansion.

As described in the background section, stents are typically inserted into a body lumen from a remote location through an insertion point in the body through which an "introducer", containing the stent in a radially compressed configuration, is threaded and navigated through the body lumen to the deployment location, where the stent is deployed in a radially expanded configuration. As referred to herein, "distal" refers to the direction further away from the insertion point and "proximal" refers to the direction closer to the insertion point. As shown in FIG. 5, stent 20 may have a first length $L_C$ when radially compressed and a second, shorter length $L_E$ when radially expanded. The "shortening ratio"

$$\frac{L_C}{L_E}$$

can be used as a measure of this change in length. Braided stents typically have a relatively large shortening ratio as compared to standard wound stents. In general, it is desirable to reduce the shortening ratio to as close to 1 as possible in order to facilitate accurate deployment and to avoid stresses on a graft attached to the stent.

The specification and claims use the terms "stent architecture" and "geometric configuration" throughout. As used herein, "stent architecture" refers to all aspects of the stent construction, including geometric configuration, dimensions, and methods of formation. There are various categories of architecture, such as, wound stent architecture, braided stent architecture, laser cut tube stent architecture, filamentary stent architecture, polygonal cell stent architecture, or zig-zag stent architecture. The various categories of stent architecture may overlap one another. For instance, one stent may comprise a filamentary, wound, polygonal cell stent architecture, whereas another stent may comprise a laser cut tube, polygonal cell stent architecture. "Filamentary" indicates that a stent comprises one or more filaments formed into the stent architecture, whereas a "laser cut tube" indicates that the stent comprises a tube that has been cut by a laser to form the geometric elements. Although there are numerous broad categories of stent architecture, within each broad category there are a number of stent architectures that are considered "different" for the purposes of this specification and claims. For example, one region of a stent having a certain height geometric element may be considered a first stent architecture whereas another region of the same stent having a similar geometric element of a different height may be considered a second, different stent architecture. Other differences in architecture from one region to another may include, for example, the number of elements in each hoop or the ratio of connected to unconnected elements between adjacent hoops.

As mentioned above, one component of stent architecture is geometric configuration. The "geometric configuration" refers to the geometric shape of the elements created within the stent. Thus, for instance, a stent having a filamentary, wound, polygonal cell stent architecture may have a geometric configuration wherein the cells are hexagonal and have a first size. Another stent having hexagonal cells of a second size still has the same geometric configuration as the stent having the hexagonal cells of the first size, but has a different stent architecture. As described herein, a stent section comprising filaments in a repeating configuration having at least one bent portion describes any of the filamentary and non-braided stents (such as those disclosed in this application) having some repeating configuration with a bent portion (i.e., either a curve or bend where the filament deviates from a linear direction as viewed when the stent is cut along its length and laid flat).

Returning now to FIG. 3, stent 10 comprises an embodiment wherein all filaments 17 are continuous filaments that extend from the wound end sections 12 into the braided middle section 14. Thus, end sections 12 and middle section 14 both have the same number of filaments, wherein the middle section consists only of filaments which also extend into the end section. In another embodiment, shown in FIG. 6, wound section 112 has a different number of filaments 17 than braided section 114. Thus, braided section 114 comprises a plurality of filaments 18 that do not extend into wound section 112. The continuous filaments extending from wound section 112 into braided section 114 may be redundant and/or tracer filaments 117. As referred to herein, a "redundant" filament or wire denotes a wire or filament that runs adjacent to another filament for some length of that element, wherein the filament to which the redundant filament runs adjacent is referred to as being an "integral" filament to the stent architecture. Thus, for instance, in FIG. 6, filaments 117 are redundant to the integral filaments 118 of the braided stent architecture of section 114. The term "tracer" is used to describe radiopaque (RO) marker filaments having a different degree of radiopacity than the surrounding filaments such that it is readily identifiable by fluoroscopic techniques. Such tracer filaments are typically redundant filaments. Although filament 117 may be a tracer filament, it may simply be a redundant, non-tracer filament. Similarly, it is possible to use any other filament, including an integral filament, such as filament 118, as a tracer filament.

Figure 6:
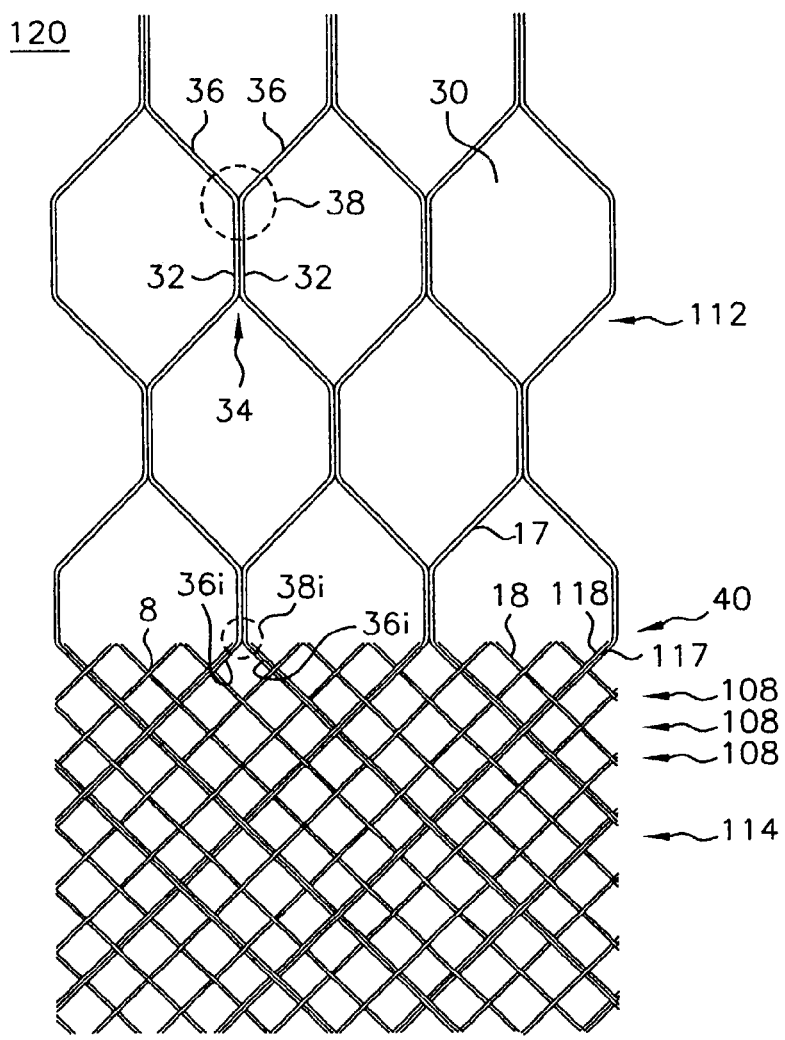
FIG. 6 is an illustration of a portion of a transition region between a polygonal cell stent section and a braided stent section where the tubular stent has been cut open along a line parallel to the stent axis and flattened.

FIG. 6 shows only the transition portion between braided section 114 and wound section 112 of a multi-section stent 120. Wound end section 112 may be at one end of stent 120 and braided section 114 may be in the middle, similar to the general layout shown in FIG. 3. In the alternative, stent 120 may have the braided and wound stent architectures at other locations within the overall stent configuration, as necessitated by the application. Furthermore, wherein a redundant filament (such as filaments 117) originates from a first stent architecture and extends into a second stent architecture, it may extend completely through both stent architectures, or only into a portion of the second architecture. For instance, such filaments may extend from a wound section 112 on one end of stent 120 as shown in FIG. 6, all the way through braided section 114, and emerge from the braided section to form a second wound section (not shown) on the other end of stent 120. In the alternative, such filaments may extend only partially from the first into the second architecture, such as extending only a limited number of rows 108 of overlaps 8 into braided section 114. Thus, for instance, braided section 114 of stent 120 as shown in FIG. 6 may extend for some distance beyond the portion of the stent shown in FIG. 6 whereas redundant filaments 117 may terminate at the length shown or at any length less than the full length of braided section 114.

Figure 19:
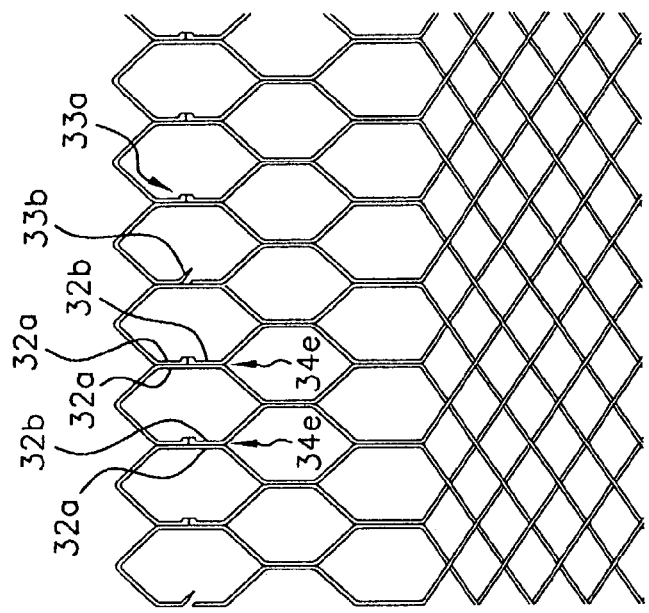
FIG. 19 is an illustration of a portion of a stent embodiment of the present invention showing the ends of certain filaments bent into protruding anchors.
Figure 18:
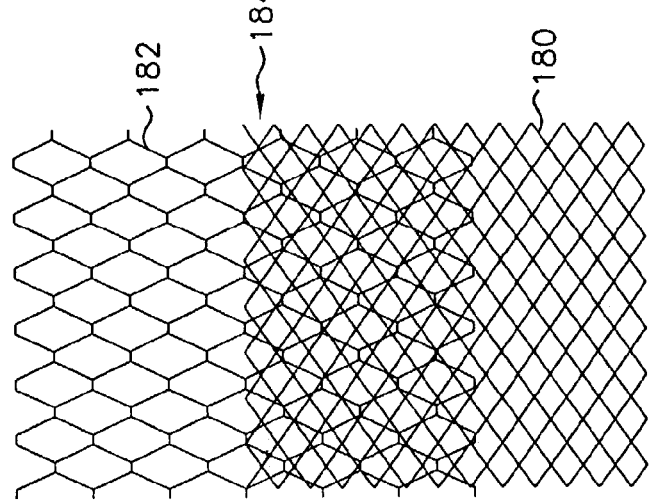
FIG. 18 is an illustration of one end of a braided stent that is anchored by a higher-radial-strength stent overlapping the braided section as is known in the prior art, where both tubular stents have been cut open along a line parallel to the stent axis and flattened.

As shown in FIG. 6, wound section 112 comprises a stent architecture having a plurality of polygonal, hexagonal cells 30 having as sides thereof straight axially-extending portions 32 joined together along a set of parallel lengths 34, the parallel lengths deviating from one another proximally and distally of each parallel length into diagonal lengths 36, such that each set of parallel lengths and attached diagonal lengths form a Y-shaped intersection 38. As shown in FIG. 6, the polygonal cell stent architecture in wound section 112 terminates at set of parallel lengths 34, which may be joined together by welding, suturing, or any means known in the art. In another embodiment, such as is shown in FIG. 3 and described herein later, the polygonal cell architecture may terminate in a zig-zag end winding. Yet another exemplary termination embodiment for a polygonal cell architecture is shown in FIG. 19.

As shown in FIG. 6, the diagonal lengths $36_i$ of each Y-shaped intersection $38_i$ at interface 40 between the wound section 112 and the braided section 114 extend from the wound section and are interwoven into the braided section as redundant filaments 117. Although not shown in FIG. 6, such filaments could also form part of the integral structure of the braided section 114, thus forming a connection between the two sections. As used herein, "integral" means necessary (non-redundant). For example, as shown in FIG. 3, the diagonal lengths 36 of each Y-shaped intersection 38 at interface 40 between wound end section 12 and braided middle section 14 extend into the wound section such that the braided section consists only of such filaments extended from the wound section. Thus, each filament 17 in each wound end section 12 continues into braided middle section 14 as a non-redundant filament 17 meshed into the braided stent architecture.

Multi-section stent embodiments in accordance with this invention having continuous wire filaments extending across the multiple sections (i.e. from the wound to the braided sections) have certain advantages, including that no further connection is required between the two stent sections. The continuous wires also provide a smooth transition between regions, rather than a sharp transition, thereby minimizing kinking. The smooth transition spreads out any strain, such as due to bending at the interface, over a continuous section of wire, rather than concentrating strain at, for instance, a weld point. Embodiments comprising only continuous wires that are integral to both the wound and braided section (such as is illustrated in FIG. 3) eliminate any loose ends that might otherwise become unraveled or pulled out of the braided configuration and/or protrude from the braided configuration in a way that can snag the body lumen or the graft.

The polygonal cell architecture shown in wound section 112 of stent 120 shown in FIG. 6 is particularly well suited for applications in which it is desired to be able to expand the stent from the compressed to the expanded configuration without a substantial degree of twist, meaning that there is no substantial change in the twisting of the stent between the radially compressed and expanded configurations. Because the polygonal cell architecture is a non-helical winding, there is substantially no inherent twisting of the stent structure between the compressed and expanded configurations. Similarly, the braided stent architecture has substantially no inherent twist as each filament oriented in one helical direction has another equivalent filament oriented in the opposite helical direction. The absence of twist is referred to herein as having no "substantial" twist because, although the braided stent and polygonal cell architectures discussed herein are not intended to have twist, some negligible but potentially measurable amount of twist may be present due to tension during the winding process or other facts. Thus, "substantially" no twist means that any twist is minimized to be essentially negligible and that there is no twist arising from stent geometry, only residual stress as may be imparted in the manufacturing process, for example.

Figure 7:
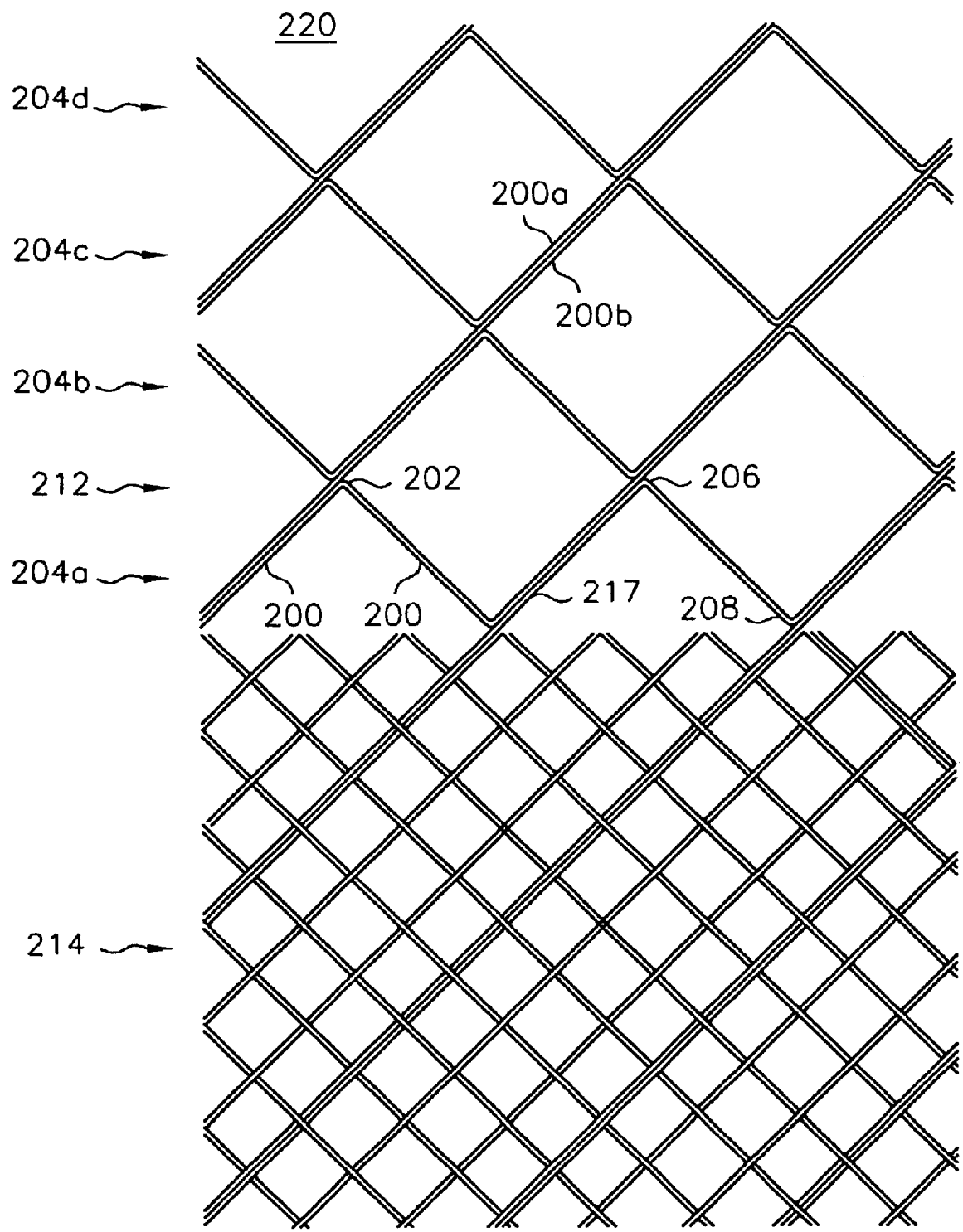
FIG. 7 is an illustration of a portion of a transition region between a zig-zag stent section and a braided stent section where the tubular stent has been cut open along a line parallel to the stent axis and flattened.

In an alternate embodiment, shown in FIG. 7, stent 220 comprises a first section 214 that has a braided stent architecture connected to a second section 212 comprising a helically wound zig-zag stent architecture. The zig-zag stent architecture comprises a plurality of struts 200 joined at apex sections 202, with a plurality of alternating oppositely-pointed apex sections arranged into hoops 204a, 204b, 204c, and 204d. Apex sections 202 pointing in a first direction can be referred to peaks 206 and apex sections pointing in the opposite direction can be referred to as a valleys 208, with any circumferentially adjacent, oppositely pointing apex sections together with three adjacent struts 200 forming a zig-zag. As shown in FIG. 7, each filament 217 of wound second section 212 extends into braided first section 214 as a redundant filament, which may be a tracer. In wound second section 212, each filament makes one full zig-zag in first hoop 204a and then extends into axially adjacent hoop 204b where it makes another full zig-zag before extending into to hoop 204c, and so on. Where one filament lies adjacent to another along struts 200a and 200b of adjacent apex sections 202a and 202b, the filaments may be joined together, such as by welding or suturing, or any means known in the art. Although four hoops 204a–d are shown in FIG. 7, any number of hoops may be constructed, as required by the application. Similarly, each filament may make more than one zig-zag before moving to the next hoop, may extend axially such that each filament skips one or more hoops before making the next zig-zag, may cross over another filament of an off-phase zig-zag, and/or may lie adjacent to another filament for a greater distance than just one strut. Thus, the zig-zag architecture shown in FIG. 7 is merely one exemplary zig-zag embodiment, but is not intended to limit the invention thereto.

Returning now to FIG. 3, wound end section 12 is a hybrid between the polygonal cell stent architecture and the zig-zag architecture. As shown in FIG. 3, wound end section 12 comprises three rows 31 of hexagonal cells 30 and terminates in an end winding 42 that comprises a zig-zag structure. As such, one of the straight axially-extending portions 32a in the end set of parallel segments 34e terminates at the end of the set of parallel segments, whereas the other straight axially-extending portion 32b continues onward to form a diagonal 36 which then forms a zig-zag 44. Where the zig-zags 44a and 44b of adjacent polygonal cells 30 overlap, they may be joined together, such as by welding, suturing, or by any means known in the art. The zig-zag end winding may comprise more than one row of zig-zags, as desired. Also, rather than being an end winding, the zig-zag structure may be intermediate a braided section and a polygonal cell section, or may be one of any number of sections having different architecture within a single, continuous stent embodiment.

A zig-zag end winding 42 may be particularly advantageous as compared to terminating wound end section 12 at set of parallel lengths 34 as shown in FIG. 6, in that the zig-zag end winding provides greater radial strength, rounds the ends, and eliminates any wires axially protruding from the end of stent 10. Thus, a zig-zag end winding 42 coupled with an embodiment without redundant filaments, such as is shown in FIG. 3, optimally minimizes any such protruding wires from the stent. The minimization of protruding wires helps to minimize potential snagging of the stent during loading and deployment of the stent and minimizes the potential for puncturing or irritating the lumen wall with the sharp, protruding wires. Minimization of protruding wires also facilitates retracting and repositioning the stent after partial deployment.

Although zig-zag end winding 42 minimizes axially protruding wires, in some applications it may be desired to provide protruding wires as anchoring hooks to help maintain the position of a stent once it is deployed in a body lumen. For example, one such end winding style, shown in FIG. 19, comprises one axially-extending portion 32a of set of parallel lengths 34e defining the end periphery of cell 30 and abutting an axially-extending portion 32b of an adjacent set of parallel lengths. The ends of portions 32a and 32b may merely be turned in toward the center of cell 30 and clipped substantially in line with the set of parallel lengths 34e (so that there are no protruding ends) as shown at termination 33a, or one of the portions, such as 32a, may instead be bent into a protruding termination 33b in the form of an anchor or hook that protrudes circumferentially from the stent. Such an anchor 33b helps to anchor the stent into the wall of the lumen (not shown) into which the stent is implanted, as is known in the art. An end winding may comprise a mixture of both the non-protruding terminations 33a and protruding terminations 33b, for example, in a pattern such as having one protruding termination after every 3 non-protruding terminations, as shown in FIG. 19.

Thus, according to the present invention, the wound section, which generally has a greater radial strength and lesser flexibility than the braided section, may, for example, comprise one or more of: a zig-zag configuration, an overlapping zig-zag configuration, a helical configuration, a non-helical configuration, or a configuration having polygonal cells. The polygonal cells may comprise, for example, hexagonal cells or overlapping hexagonal cells. These geometric configurations are not limiting, however, as any filamentary stent architecture comprising any geometric configuration known in the art may be used. The filaments or wires that comprise the braided section may comprise only filaments that extend into and are integral to the wound section, or the braided section may have additional filaments that do not extend into the wound section. The filaments from the wound section may extend into the braided section as non-redundant elements of the braided section, or may extend into the braided section as redundant filaments. One or more wound sections may comprise end sections so connected to braided sections, or the wound or braided sections may be located anywhere along the length of the stent.

Within the various combinations and permutations of known stent architecture variables, any number of embodiments are possible. The length and/or architecture of the wound section can be tailored to each application to provide the radial strength desired. The several embodiments shown in FIGS. 3 and 6–9 and/or described below, therefore, are only exemplary and are not intended to be limiting. Thus, for example wound section 112 as shown in FIG. 6 consisting of polygonal cells 30 with no zig-zag end winding may be combined with braided section 14 as shown in FIG. 3. In such case, diagonals 36 extending from Y-shaped intersection 38 at interface 40 of the wound stent architecture 112 as shown in FIG. 6 extend into braided stent architecture 14 as non-redundant elements of the braided stent architecture 14 as shown in FIG. 3, rather than as redundant elements as shown in FIG. 6. Furthermore, the combination of stent architectures is not limited to only two types of architectures, such as one wound section connected to one braided section, or even three different stent architectures, such as a braided section connected to a polygonal cell section with a zig-zag end winding, but rather may comprise any number of different architectures in combination as needed to meet the needs of the specific application.

Figure 8:
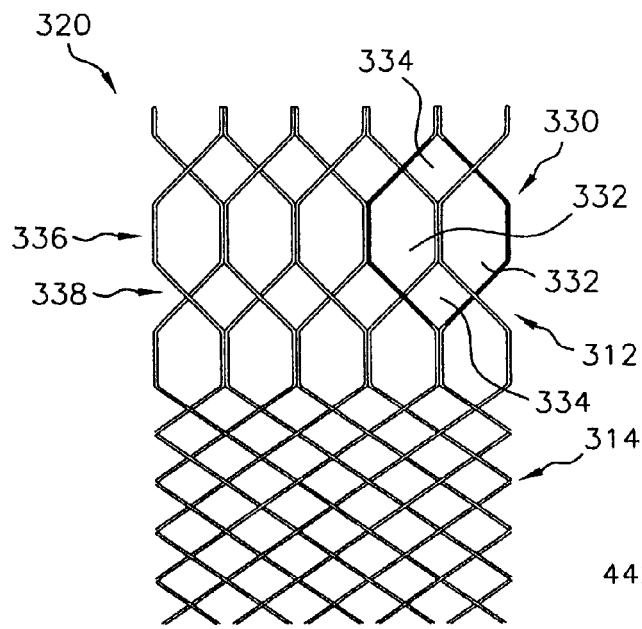
FIG. 8 is an illustration of a portion of a transition region between an overlapping polygonal cell stent section and a braided stent section where the tubular stent has been cut open along a line parallel to the stent axis and flattened.
Figure 10:
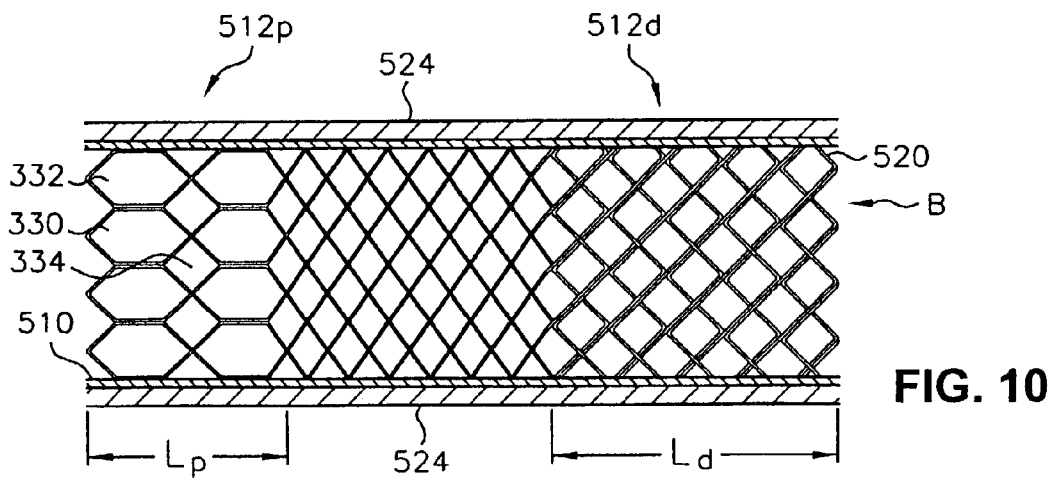
FIG. 10 is an illustration of an exemplary embodiment of a stent and attached graft implanted within a lumen according to the present invention, the stent having different stent architectures and lengths in its distal and proximal wound sections, with the lumen and graft shown in cross-section.

As shown in FIG. 8, the polygonal cells 330 in wound section 312 of stent 320 may overlap one another. The large overlapping hexagonal polygonal cells 330 thus circumferentially bisect each other into four sub-cells—two hexagonal sub-cells 332 and two diamond-shaped sub-cells 334 to create rows 336 (or hoops when in tubular form) of hexagons alternating with rows 338 of diamonds. Although shown in FIG. 8 wherein braided section 314 does not comprise redundant filaments, an alternate embodiment may be constructed with redundant filaments. The overlapping cell architecture may be further modified by adding a zig-zag end winding, such as end winding 42 as shown in FIG. 3. Depending where the end winding is positioned axially, however, the resulting wound section may have only partial or full large hexagonal cells 330 and greater or fewer rows 336 of hexagonal sub-cells 332 or rows 338 of diamond sub-cells 334 than as shown in FIG. 8. For example, section 512p in FIG. 10 illustrates such an overlapping call architecture having a zig-zag end winding, where only partial large hexagonal cells 330 are present.

The many permutations include a stent comprising a wound section 212 having a zig-zag stent architecture such as is shown in FIG. 7, except that filaments 217 extend from wound section 212 into braided section 214 as non-redundant filaments such as is shown in FIG. 3, rather than as redundant filaments as shown in FIG. 7. Thus, a braided section 14 as shown in FIG. 3 may consist only of filaments 17 that extend between and are integral to both the braided section 14 and a zig-zag wound section similar to section 212 shown in FIG. 7.

Figure 9:
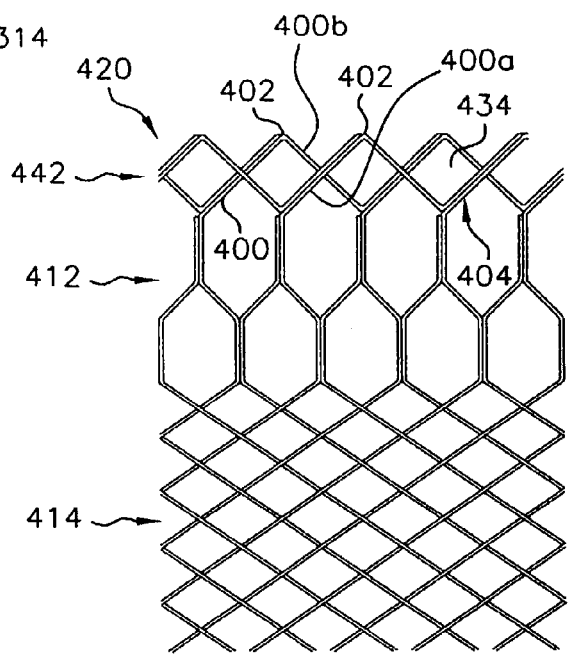
FIG. 9 is an illustration of a portion of a transition region between a hybrid polygonal cell/overlapping zig-zag stent section and a braided stent section where the tubular stent has been cut open along a line parallel to the stent axis and flattened, and the overlapping zig-zag end winding comprises sets of double filaments that are parallel to one another.

As shown in FIG. 9, stent 420 may comprise a wound section 412 comprising a hybrid polygonal cell and zig-zag architecture wherein the zig-zag end winding 442 is an overlapping zig-zag structure. In an overlapping zig-zag structure, as shown in FIG. 9, adjacent zig-zags circumferentially bisect one another, such that each strut 400a of a first zig-zag approaching an apex section 402 pointed in one direction crosses over another strut 400b of a second zig-zag coming from a circumferentially-adjacent apex section 402 pointed in the same direction, creating a row of diamond-shaped cells 434. In any of the hybrid hexagonal cell/zig-zag or hexagonal cell/overlapping zig-zag structures, the number of rows of hexagonal cells to zig-zag or overlapping zig-zag rows may be varied, with an equal number of rows of each type or more rows of one type than the other. A zig-zag and overlapping zig-zag architecture could also be combined. Although shown in FIG. 9 wherein braided section 414 does not comprise redundant filaments, an alternate embodiment may be constructed with redundant filaments.

Figure 21:
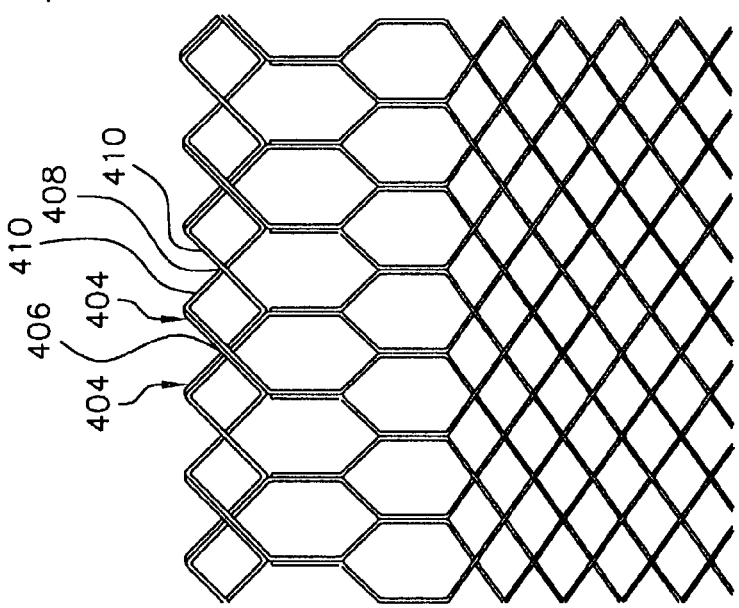
FIG. 21 is an illustration of a portion of a transition region between a hybrid polygonal cell/overlapping zig-zag stent section and a braided stent section where the tubular stent has been cut open along a line parallel to the stent axis and flattened, and the overlapping zig-zag end winding comprises sets of double filaments that intersect one another.

The overlapping zig-zag structure shown in FIG. 9 provides sets of double filaments 404 extending parallel to one another. Such a configuration may impart a twisting force upon expansion of the stent, which may be undesirable for certain applications. Therefore, to minimize any twisting forces, another embodiment of the overlapping zig-zag structure, shown in FIG. 21, may be constructed. As shown in FIG. 21, the overlapping zig-zag structure is similar to that shown in FIG. 9, except that the double filaments 404 cross over one another, providing a pattern consisting of sets 406 of crossed double filaments 404 alternating with sets 408 of crossed single filaments 410. As such, for each set of double filaments oriented in one direction, there is a set of double filaments oriented in the opposite direction such that any twisting forces are counteracted.

Although stent 10 depicted in FIG. 3 having wound end sections 12 and a braided middle section 14 shows identical end sections 12 having equal lengths $L_{12}$, an equal number of rows of polygonal cells 30, and the same stent architecture, a stent may also be constructed wherein each wound end section is different. For example, as shown in FIG. 10, because stent 520 is implanted with its distal end section 512$d$ upstream from proximal end section 512$p$ relative to blood flow along arrow B inside lumen 524, it is often desirable to have an especially effective seal between the graft covering 510 of stent 520 and the walls of lumen 524 to prevent blood from seeping between the graft and the lumen. A key factor in the effectiveness of the seal is the radial strength exerted by distal end section 512$d$ against lumen 524. Because the dynamic pressure exerted by the blood flow attempting to seep between graft 510 and lumen 524 is strongest at the distal end section 512$d$, a higher overall radial strength may be required at the distal end section 512$d$ than at the proximal end section 512$p$. Thus, stent 520 may have a different stent architecture (for example, a zig-zag end winding) in the distal end section than at the proximal end section, or the end sections may have the same stent architecture with a longer length $L_d$ of the distal end section than length $L_p$ of the proximal end section. As shown in FIG. 10, wound section 512$d$ has a different architecture than section 512$p$ and a length $L_d$ that is longer than length $L_p$. In an alternative embodiment, a stent may have a wound end section only on one end, for example the upstream end, and no wound section at the opposite end.

Figure 11:
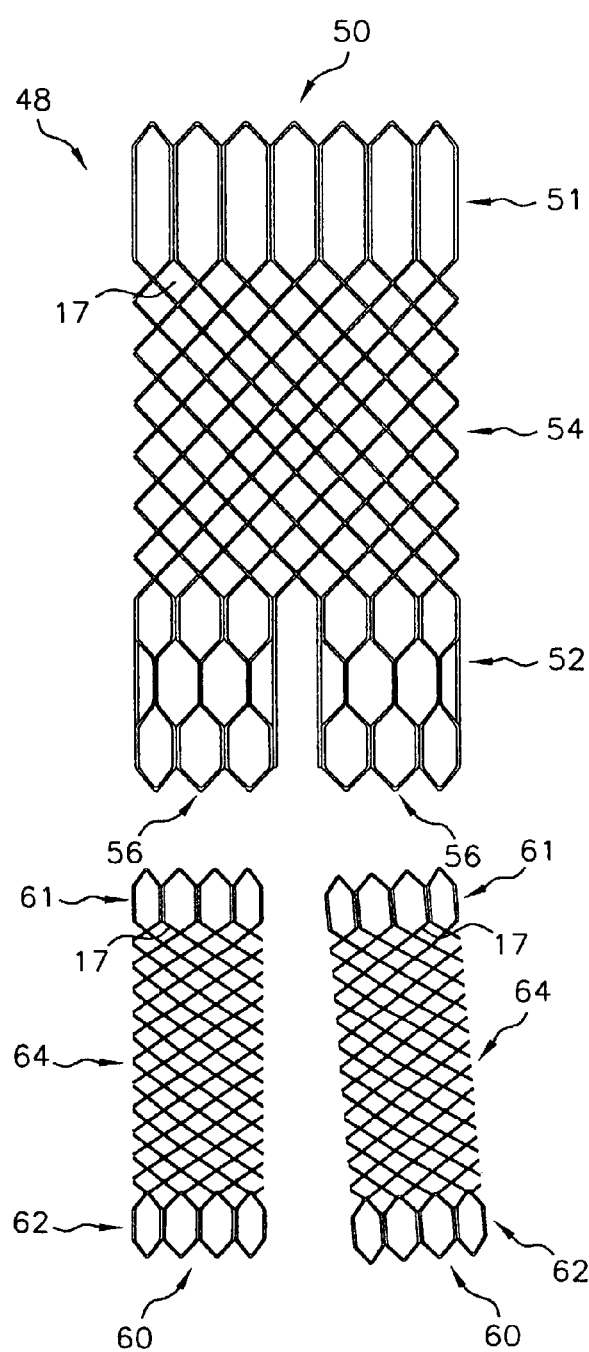
FIG. 11 is a side view illustration of a three-piece modular bifurcated stent according to the present invention.

The various multi-section stents as described herein may be particularly well-suited to the construction of modular stents adapted for assembly in situ. Such modular stents comprise at least two modular components. For example, as shown in FIG. 11, modular stents are frequently used in applications directed for implantation in branching lumen, such as for repairing aneurysms of the aorta in the section of the aorta which branches into the right and left iliac arteries. Non-bifurcated modular stents are used in non-branching lumen. Thus, although discussed herein with respect to the bifurcated stent shown in FIG. 11, multi-section stents of the present invention may be applied to non-bifurcated modular stents as well.

As shown in FIG. 11, modular stent 48 comprises trunk component 50 and at least one modular leg component 60. Trunk component 50 further comprises a multi-section stent of the present invention in which there is a braided middle section 54 and a wound distal end section 51 and wound proximal end section 52. The wound proximal end section 52 of trunk component 50 is bifurcated into two connection sockets 56. Each leg component 60 similarly comprises a braided middle section 64 and a wound distal end section 61 and wound proximal end section 62. Thus, the braided middle sections of both components have a greater flexibility than the wound end sections, and the wound end sections have a greater radial strength than the braided middle section. In accordance with the present invention, each component 50 and 60 has at least one continuous filament 17 integral to both the braided and wound sections. As each component also has a radially compressed configuration and a radially expanded configuration, the braided stent architecture generally tends to have a shortening ratio that is greater than the shortening ratio of the wound stent architecture. Leg component 60 is adapted to be fitted together with trunk component 50 such that distal end sections 61 of the leg component interlocks inside proximal end section 52 of the trunk component into one of the sockets 56.

Figure 12:
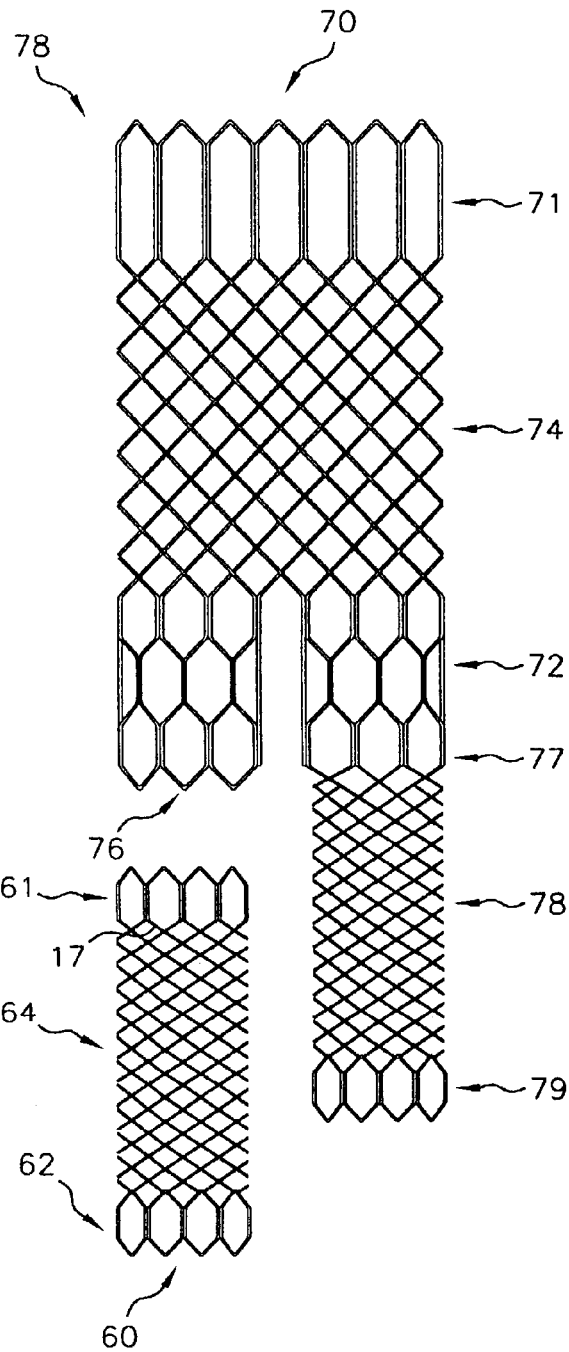
FIG. 12 is a side view illustration of a two-piece modular bifurcated stent according to the present invention.

Bifurcated stent embodiments of the present invention may resemble stent 48 shown in FIG. 11, wherein there are two leg components 60 that each interlock inside the connection sockets 56 of the proximal end section 52 of the trunk component, or may resemble stent 78 as shown in FIG. 12. Stent 78 comprises a trunk component 70 having a distal end section 71, a trunk middle section 74 connected to the trunk distal end section 71, a trunk bifurcated section 72 connected to the trunk middle section and branching into a contralateral socket 76 and an integral leg transition 77. The integral leg transition is connected to an integral leg middle section 78 which is connected to an integral leg proximal end section 79. Modular leg component 60 of stent 78 is similar to the modular leg component described for stent 48 as shown in FIG. 11. Instead of having two modular legs as shown in FIG. 11, however, stent 78 has only a single leg 60 that connects into contralateral socket 76 of trunk component 70.

The use of multi-section stents of the present invention in bifurcated applications has certain advantages over bifurcated stents having other configurations. For example, bifurcated stents are typically used to treat aortic aneurysms and thus often incorporate a graft covering. Because of the large shortening ratio common to braided stent designs, the use of braided stents having graft coverings requires graft coverings that can accommodate shortening. Although such accommodating graft coverings are known, the use of braided stents in a bifurcated region, such as trunk bifurcated section 72, creates a complex geometry that complicates the pairing of graft to stent. Furthermore, the process for creating bifurcated regions using a braided stent may also be somewhat more complex than that for creating such a region using a wound stent. Thus, any complexities of using a braided architecture in a bifurcated region may be avoided by the use of a wound stent architecture in the bifurcated region of such a stent.

Additionally, because the present invention enables tailoring of different sections of a stent for different radial strength and flexibility, two- or three-piece bifurcated designs such as are shown in FIGS. 11 and 12 can be designed with a relatively short trunk section socket. The relatively short socket length is possible because the overall radial force needed to create a seal where the modular leg overlaps the inside of the trunk section socket can be distributed over a smaller surface area of contact using a higher radial strength stent section. Overlapping sections tend to be less flexible than non-overlapping sections, and may be subject to kinking. Thus, potential kinking due to overlapping stents sections can be reduced via minimizing the length of the overlapping section. A shorter socket length enables a shorter overall trunk length and longer, more flexible leg sections.

Although the modular stent embodiments shown in FIGS. 11 and 12 comprise wound end sections (i.e. sections 51, 56, 61, and 62 in FIG. 11 and sections 61, 62, 71, 72 and 79 in FIG. 12) with a common stent architecture, or at least a common geometric configuration, and middle sections (i.e. sections 54 and 64 in FIG. 11 and sections 54, 75, and 78 in FIG. 12) having a common braided architecture, each individual section may have a different stent architecture, including a different geometric configuration.

Figure 13:
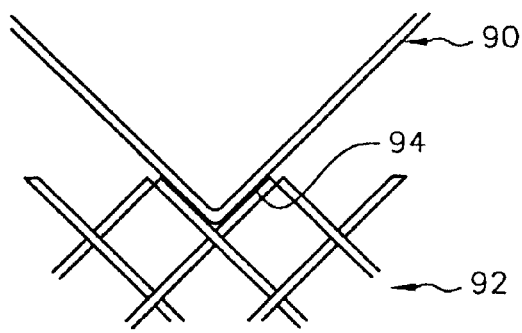
FIG. 13 is an illustration of a portion of a transition region between a zig-zag stent section and a braided stent section showing a weld joining the two different stent sections.
Figure 14:
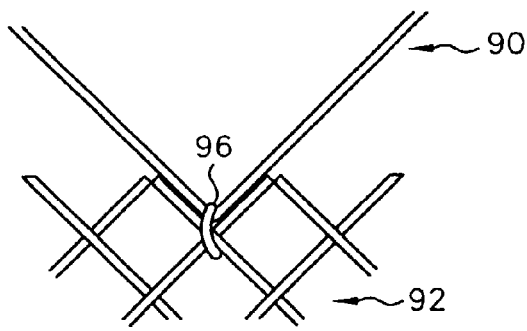
FIG. 14 is an illustration of a portion of a transition region between a zig-zag stent section and a braided stent section showing a suture joining the two different stent sections.

Several embodiments of wound filament stent architectures joined with braided filament stent architectures have been described above wherein each embodiment included a continuous filament which extends between both the wound and braided architectures for connecting the two stent sections. Other joining means can also be provided. FIGS. 13–16 show portions of different embodiments of an exemplary transition region between a zig-zag stent architecture section 90 and a braided stent architecture section 92. As shown in FIG. 13, braided section 92 may be connected to the wound section 90 by a weld 94. Instead, as shown in FIG. 14, braided section 92 and wound section 90 may be connected by a suture 96.

Figure 15:
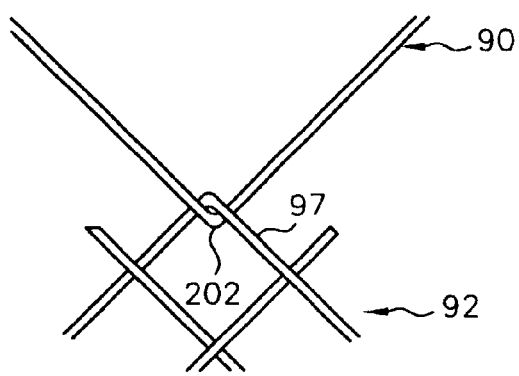
FIG. 15 is an illustration of a portion of a transition region between a zig-zag stent section and a braided stent section showing a filament of the braided section looping around an apex section of the zig-zag section to join the two sections.
Figure 16:
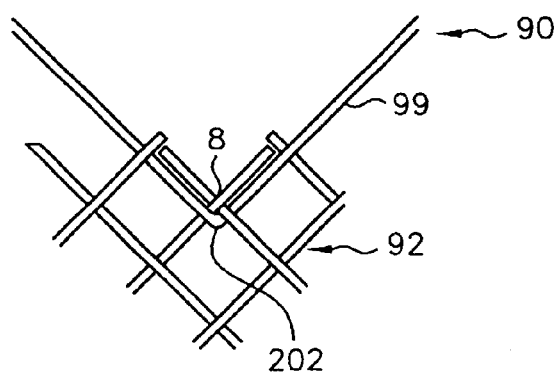
FIG. 16 is an illustration of a portion of a transition region between a zig-zag stent section and a braided stent section showing a filament of zig-zag section looping around an overlap in the braided section to join the two sections.

In another embodiment, as shown in FIG. 15, a filament 97 of braided section 92 may be looped around an apex section 202. Filament 97 may be a continuous filament that is interwoven into braided section 92, or two filaments welded together where the filaments meet after looping through apex section 202. Filament 97 may be interwoven through the entire length of braided section 92 as a redundant or non-redundant member, or may extend through only a portion of the braided section 92 as a redundant member. Rather than a filament of the braided section looping through the wound section, a filament 99 which forms apex section 202 of wound section 90 may be looped around an overlap 8 in braided section 92, as shown in FIG. 16. Additionally, any of the configurations shown in FIGS. 13–16 may be combined.

Figure 17:
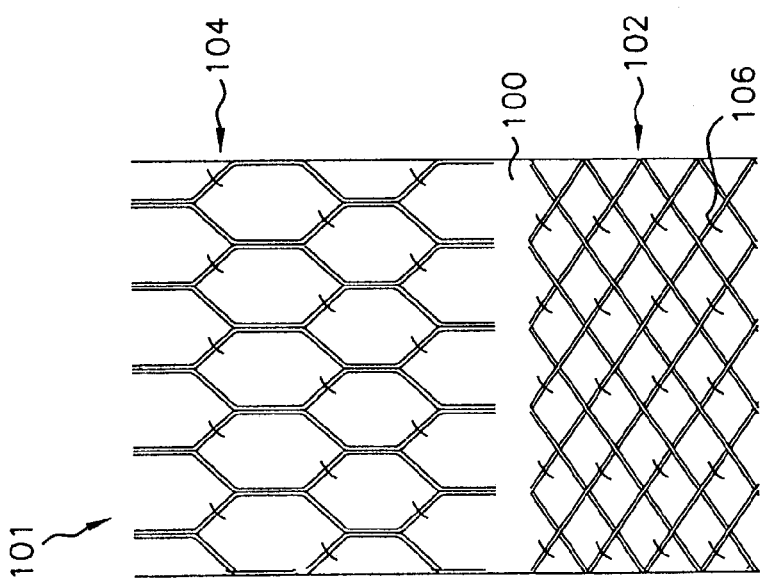
FIG. 17 is an illustration of a multi-section stent embodiment according to the present invention wherein the wound stent section and a braided stent section are connected together by a common graft, where the tubular stent has been cut open along a line parallel to the stent axis and flattened.

As shown in FIG. 17, where stent 101 comprises a common graft 100 attached to both braided section 102 and wound section 104 of the stent, the common graft may provide the connection between the braided section and the wound section. Graft 100 may be connected to stent 101 by, for example, sutures 106 as shown in FIG. 17, or by staples, adhesive bonds, or any means known in the art. Stent 101 and attached graft 100 shown in FIG. 17 are illustrated with the tubular stent/graft combination cut along a line parallel to the stent axis and flattened, with the stent shown overlying the graft. Graft 100 may be an outer covering for stent 101, in which case FIG. 17 shows an internal view, or graft 100 may be an inner liner for stent 101, in which case FIG. 17 shows an external view.

Although the use of stents generally is widespread in endovascular applications where the stent is deployed in a blood vessel, this invention may also be beneficial for applications in other body lumen. The advantages inherent in this invention, which combines the flexibility found in braided stent architectures with the secure anchoring force and stent-end patency provided by wound stent architectures, are particularly well-suited for applications in any tortuous lumen. Thus, for instance, this invention may be advantageous for use in enteral applications that require flexibility to conform to a tortuous intestine but that also require strong anchoring forces to hold the stent in place. Additionally, the treatment of ostial lesions, such as in bilary or renal applications, where strong anchoring and radial strength is particularly needed at the end of the stent, may also benefit from this invention. Therefore, this invention is applicable to a broad range of stent diameters, from femoral applications in the 6 mm range and iliac applications in the 8 mm range, to aortic trunk applications in the 34 mm range and thoracic applications in the 45 mm range.

Although described herein with respect to certain specialized embodiments, such as embodiments for treating abdominal aortic aneurysms (AAA) or for providing greater radial strength at the ends of a stent for anchoring, the present invention may be applied across a broad range of applications. An important advantage offered by this invention, is that it allows controlled tailoring of the radial strength of a particular portion of a stent as necessary to meet an application. Therefore, although providing ends with greater strength may be one application, the invention may be used to provide controlled radial strength in any portion of the stent, including to provide lesser strength in certain sections if desired. For example, referring now to FIG. 22, to facilitate the conformance of a stent 700 to one or more known tortuous regions 702 in a lumen 704 into which the stent is to be implanted, the stent may be designed with one or more relatively flexible sections, such as braided section 706 as compared to wound sections 708, to align with the tortuous region. Wound sections 708 are not necessarily end sections, and thus stent 700 may further comprise other flexible regions therein, for example, to accommodate other tortuous regions of lumen 704.

In yet another embodiment, the invention may be used to provide the same degree of radial strength across the entire length of a stent, rather than to provide an increased or decreased radial strength in some portion. For example, a wound end section on a braided stent may be provided to counteract a lesser radial strength that would otherwise be present at the ends of a particular stent architecture. For example, braided stents have a known end effect wherein the radial strength at the ends of the braided architecture is less than in the middle. This problem is sometimes addressed by flaring the braided ends (so that when compressed to the same diameter as the rest of the stent, the radial force exerted is the same). In accordance with this invention, however, a wound end section may be provided at the end of the braided section to provide the same degree of radial strength across the entire length of the stent, or at least a greater degree of radial strength in the end section than would otherwise be present due to the end effect. Such a wound end section may or may not be flared. Such a stent may have a superficial appearance similar stent embodiments described and illustrated herein, such as, for example, stent 10 as shown in FIG. 3, but having fewer rows 31 of cells 30 and no end winding 42, such that the radial strength of end 12 is only sufficient to counteract the end effect of braided section 14, but not to provide greater strength than the remainder of the stent.

Figure 20:
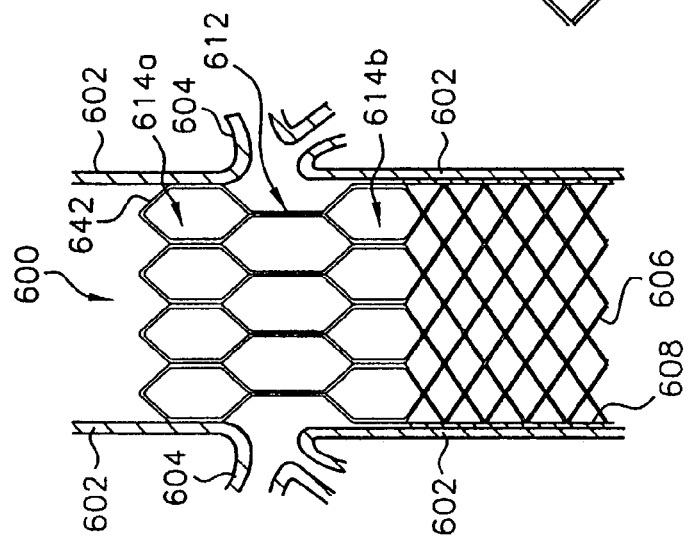
FIG. 20 is a cross-sectional illustration of a portion of a stent embodiment of the present invention shown implanted in an aorta bridging the renal arteries.

The unlimited combinations of different filamentary stent architectures in accordance with the present invention may be beneficial not just because such combinations enable control of the radial force at various points along the length of the stent, but also because such combinations may provide other structural advantages. For example, referring now to FIG. 20, there is shown an embodiment wherein a stent 600 is implanted in a region of an aorta 602 adjacent intersecting renal lumen 604. Although braided section 606, which may have a graft covering 608, is desirable for its flexibility below and above renal lumen 604, the dense, close-knit structure of the braided section, having a first percentage of open area, would block blood flow into the renal lumen if it extended across them, even without covering 608. In fact, in some cases, lumen of lesser physiological importance than renal lumen 604 (for example, capillaries that provide redundant vascular pathways to areas that can be served by other pathways) are intentionally covered in the process of treating an aneurysm or other problem in the main lumen with a graft-lined or covered stent. To prevent covering "important" intersecting lumen (lumen that cannot be covered without potentially serious impact to the patient) such as lumen 604, wound section 612, having a polygonal geometry with a second percentage of open area greater than the first percentage, is provided in the portion of the stent implanted adjacent renal lumen 604. As shown in FIG. 20, wound section 612 has an even greater percentage of open area than sections 614a and 614b of polygonal architecture above and below it, respectively. Section 612, as shown in FIG. 20, comprises a geometric configuration that is elongated, but essentially similar, to sections 614a and 614b. Section 614a also comprises a zig-zag end winding 642. The polygonal stent structure having a greater percentage of open area provides negligible obstruction of blood flow into the renal lumen. Although greater radial strength may be provided in polygonal architecture section 612 as compared to braided section 606, section 612, because of its elongated shape, has a lesser radial strength than sections 614a and 614b. In certain applications such differences in radial strength may not be necessary or desired, but rather the greater percentage of open area in the stent architecture adjacent the renal branches may be the advantageous difference sought between the sections of different architecture.

"Percentage of open area" as used herein may be defined as:

$$\frac{A_s - \sum A_{fp}}{A_s} = \frac{(\pi D_s L_s - \sum D_f L_f)}{\pi D_s L_s}$$

where:
$A_S$=the cylindrical surface area of the stent ($\pi D_S L_S$)
$L_S$=the length of the stent portion at issue
$D_S$=the diameter of the stent
$\Sigma A_{fp}$=the "projected" rectangular area ($D_f L_f$) of each filament onto $A_S$
$D_f$=the diameter of the filament
$L_f$=the length of the filament contained within length $L_S$ It should be noted that the projected area $A_{fp}$ is not the same as the actual surface area of each filament length $L_f$, which is equal to projected area $A_{fp}$ times $\pi$.

The methods of constructing the various braided and wound stent architectures are well known in the art. For example, the method for constructing the polygonal cell stent architecture is described in U.S. Pat. No. 5,540,712 to Kleshinski et al. and essentially comprises winding the stent around pins on a mandrel. The weaving of filaments together into a braid is a well-known operation, not just in the medical field, but also in textile manufacture. Combining the braided and wound architectures can be undertaken by providing first a braided stent by means known in the art and leaving loose filaments protruding from one or both ends. These loose filaments can then be wound around pins on a mandrel to make the wound section. In the alternative, a wound section can be first constructed and then the loose ends protruding from that section braided, and then optionally, the loose ends protruding from the braided section wound around a mandrel into another wound section. Where, for instance a bifurcated stent such as is shown in FIG. 17 is constructed, alternation between winding operations and braiding operations may occur numerous times until all the requisite sections have been completed to meet the application needs.

Although certain combinations of braided and wound stent architectures have been described extensively herein, other combinations of stent architectures, each having different flexibility, radial strength, or shortening characteristics may be combined in accordance with this invention. Furthermore, although polygonal cell and zig-zag wound stents have been described specifically herein, other wound stent constructions may also be acceptable for combination with braided stent architectures. For example, a wound stent architecture similar to that shown in sections 112 of FIG. 6 may be constructed with polygonal cells 30 rotated by 90 degrees such that parallel lengths 34 align circumferentially rather than axially. Also, wound stent architectures as described in the following U.S. patents and patent families claiming priority therefrom may be well-suited for combination with braided stent designs by one or more of the methods described herein, the following list of U.S. patents being only exemplary, not limiting:

| | |
|---|---|
| 5,019,090 | Pinchuk |
| 5,135,536 | Hillstead |
| 5,292,331 | Boneau |
| 5,282,824 | Gianturco |
| 5,354,308 | Simon et at. |
| 5,507,767 | Maeda et at. |
| 5,800,515 | Nadal et at. |

Although a braided stent configuration is discussed herein extensively as an exemplary flexible architecture, other flexible stent architectures known in the art may also be used. Thus, generally, the present invention comprises a multi-section filamentary stent comprising a first section, having a first stent architecture comprising one or more filaments in a first geometric configuration, and a second section, having a second stent architecture comprising one or more filaments in a second geometric configuration. The first stent architecture has a first flexibility and a first radial strength, and the second stent architecture has a second flexibility less than the first flexibility and a second radial strength greater than the first radial strength. The stent comprises at least one continuous filament integral to both the first and second sections. The first geometric configuration is substantially different from the second geometric configuration. In another embodiment, the first and second stent architectures may differ in percentage of open area, but not necessarily differ in radial strength or flexibility. In yet another embodiment, the first and second stent architectures may have the same radial strength and flexibility wherein the second architecture merely compensates for an end effect in the first stent architecture that would otherwise provide a lesser radial strength at the end.

Figure 22:
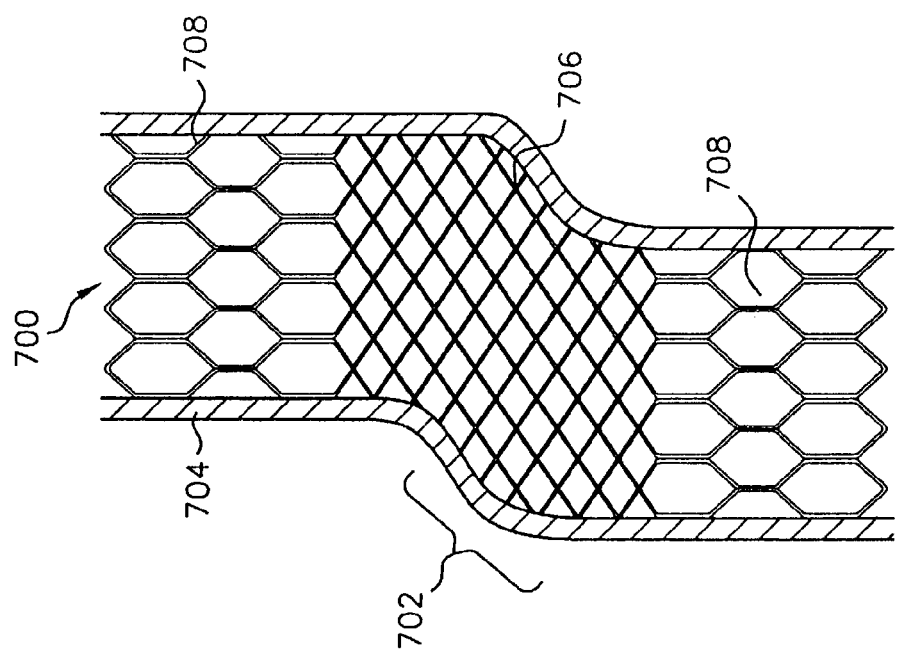
FIG. 22 is an illustration of a portion of a stent embodiment of the present invention shown implanted in a lumen having a tortuous region, the lumen shown in cross-section.

In addition to the various structures disclosed herein, the invention also comprises methods for treating a body lumen, the method comprising implanting any one of the stent structures described herein. In particular, one treatment method may comprise implanting one of the structures described herein with a higher-radial-strength segment at one or both ends of the stent, especially on the upstream end of the stent, as is shown in FIG. 10. Another treatment method may comprise implanting a more flexible region aligned with a tortuous region of a lumen as shown in FIG. 22. Another treatment method may comprise implanting a stent according to this invention from a compressed to an extended configuration without imparting a twisting motion to the stent. Yet another method may comprise implanting a segment having a greater percentage of open area adjacent to a region of the lumen having intersecting lumen, as is shown in FIG. 20. Finally, the invention also comprises a method of counteracting an end effect of a braided stent by incorporating a wound section onto the end of the braided stent, as described herein.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A modular stent comprising at least two modular components adapted to be joined together in situ:
   a first modular component comprising a multi-section stent comprising a first section, having a braided first stent architecture and a first geometric configuration with a first flexibility and a first radial force, and a second section, having a wound second stent architecture and a second geometric configuration with a second flexibility less than the first flexibility and a second radial force greater than the first radial force, the first component comprising at least one continuous filament contained in both the first and second sections; and
   a second modular component comprising a multi-section filamentary stent comprising a third section, having a braided third stent architecture and a third geometric configuration and a fourth section, having a wound fourth stent architecture in a fourth geometric configuration, the second component comprising at least one continuous filament contained in both the third and fourth sections.

2. The modular stent of claim 1 wherein the stent has a radially compressed configuration and a radially expanded configuration, the first stent architecture having a first shortening ratio, the second stent architecture having a second shortening ratio, the third stent architecture having a third shortening ratio, and the fourth stent architecture having a fourth shortening ratio.

3. The modular stent of claim 1 wherein the third geometric configuration is similar to the first geometric configuration and the fourth geometric configuration is similar to the second geometric configuration.

4. The modular stent of claim 3 wherein the third stent architecture is identical to the first stent architecture and the fourth stent architecture is identical to the second stent architecture.

5. The modular stent of claim 4 wherein the first component and the second component each comprise a middle section having the first stent architecture positioned between two end sections each having the second stent architecture, and in which the first component is adapted to be fitted together with the second component such that one of the end sections of the first component interlocks inside one of the end sections of the second component.

6. The modular stent of claim 5 wherein the modular stent is a bifurcated stent wherein:
   the first modular component comprises a trunk component comprising a trunk distal end section, a trunk proximal end section, and a trunk middle section connected between the trunk distal end section and the trunk proximal end section, the trunk proximal end section being bifurcated into two connection sockets; and
   the second modular component comprises a leg component comprising a leg distal end section, a leg proximal end section, and a leg middle section connected between the leg distal end section and the leg proximal end section, the leg distal end section adapted to interlock inside one of the connection sockets of the trunk proximal end section;
   wherein the trunk middle section and the leg middle section each comprise the first stent architecture, and the trunk distal end section, the trunk proximal end section, the leg distal end section, and the leg proximal end section each comprise the second stent architecture.

7. The modular stent of claim 5 wherein the modular stent is a bifurcated stent comprising:
   a trunk component comprising a trunk distal end section, a trunk middle section connected to the trunk distal end section, a trunk bifurcated section connected to the trunk middle section and branching into a contralateral socket and an integral leg transition, the integral leg transition connected to an integral leg middle section which is connected to an integral leg proximal end section; and
   a modular leg component comprising a modular leg distal end section, a modular leg proximal end section, and a modular leg middle section connected between the modular leg distal end section and the modular leg proximal end section, the modular leg distal end section adapted to interlock inside the contralateral socket of the trunk bifurcated section;
   wherein the trunk middle section, the integral leg middle section, and the modular leg middle section comprise the first stent architecture, and the trunk distal end section, the trunk bifurcated section, the integral leg proximal end section, the modular leg distal end section, and the modular leg proximal end section comprise the second stent architecture.

8. The modular stent of claim 1 wherein the modular stent is a bifurcated stent wherein:
   the first modular component comprises a trunk component comprising a trunk distal end section, a trunk proximal end section, and a trunk middle section connected between the trunk distal end section and the trunk proximal end section, the trunk proximal end section being bifurcated into two connection sockets;
   the second modular component comprises a leg component comprising a leg distal end section, a leg proximal end section, and a leg middle section connected between the leg distal end section and the leg proximal end section, the leg distal end section adapted to interlock inside one of the connection sockets of the trunk proximal end section.

9. The modular stent of claim 8 wherein the trunk middle section and the leg middle section each comprise braided stent architectures, and the trunk distal end section, the trunk proximal end section, the leg distal end section, and the leg proximal end section each comprise wound stent architectures.

10. The modular stent of claim 9 further comprising a third component adapted to interlock inside the other of the connection sockets of the trunk proximal end section.

11. The modular stent of claim 1 wherein the modular stent is a bifurcated stent comprising:

a trunk component comprising a trunk distal end section, a trunk middle section connected to the trunk distal end section, a trunk bifurcated section connected to the trunk middle section and branching into a contralateral socket and an integral leg transition, the integral leg transition connected to an integral leg middle section which is connected to an integral leg proximal end section;

a modular leg component comprising a modular leg distal end section, a modular leg proximal end section, and a modular leg middle section connected between the modular leg distal end section and the modular leg proximal end section, the modular leg distal end section adapted to interlock inside the contralateral socket of the trunk bifurcated section.

* * * * *